United States Patent
Ramamoorthy et al.

(10) Patent No.: US 6,611,327 B2
(45) Date of Patent: Aug. 26, 2003

(54) DETECTION OF CONTAMINANTS ON LOW WAVELENGTH MASKS

(75) Inventors: Arun Ramamoorthy, Sunnyvale, CA (US); Giang Dao, Austin, TX (US); Christopher Gerth, Santa Clara, CA (US)

(73) Assignee: Intel Corporation, Santa Clara, CA (US)

(*) Notice: Subject to any disclaimer, the term of this patent is extended or adjusted under 35 U.S.C. 154(b) by 23 days.

(21) Appl. No.: 09/817,012

(22) Filed: Mar. 23, 2001

(65) Prior Publication Data

US 2002/0135759 A1 Sep. 26, 2002

(51) Int. Cl.[7] ................................. G01N 21/88
(52) U.S. Cl. ......................... 356/237.4; 356/73
(58) Field of Search .............. 356/237.2, 237.3, 356/237.4, 237.5, 301, 72, 73; 250/559.45, 559.46, 338.1, 339.11, 339.12

(56) References Cited

U.S. PATENT DOCUMENTS

| | | | | |
|---|---|---|---|---|
| 4,760,265 A | * | 7/1988 | Yoshida et al. | 250/358.1 |
| 5,179,422 A | * | 1/1993 | Peterson | 250/559.41 |
| 5,377,003 A | * | 12/1994 | Lewis et al. | 250/339.02 |
| 5,528,368 A | * | 6/1996 | Lewis et al. | 250/339.02 |
| 5,841,139 A | * | 11/1998 | Sostek et al. | 250/339.05 |
| 6,177,993 B1 | * | 1/2001 | Sommargren | 356/337 |
| 6,226,082 B1 | * | 5/2001 | Roe | 250/339.12 |
| 6,266,137 B1 | * | 7/2001 | Morinaga | 356/237.1 |
| 6,274,385 B1 | * | 8/2001 | Hochlowski et al. | 250/339.11 |
| 6,279,147 B1 | * | 8/2001 | Buynoski et al. | 430/5 |
| 2002/0074517 A1 | * | 6/2002 | Krutchinsky et al. | 250/492.1 |

* cited by examiner

Primary Examiner—Thien M. Le
Assistant Examiner—Uyen-Chau N. Le
(74) Attorney, Agent, or Firm—Fish & Richardson P.C.

(57) ABSTRACT

Testing of a mask which is intended to be used for low wavelength lithography. At lower wavelengths, e.g., 157 nm, certain contaminants may become visible, even though they were transparent under visible or ultraviolet light. A combination of Raman spectroscopy and infrared absorption spectroscopy are used to identify the contaminants.

24 Claims, 3 Drawing Sheets

DETECTION OF CONTAMINANTS ON LOW WAVELENGTH MASKS

BACKGROUND

Lithography is often used to form features on a substrate. Generation of smaller features may use shorter wavelengths. Lithography may use, for example, a 157 nm wavelength lithographic light. Light of this wavelength, and other similar short wavelengths e.g. 126 nm, may present new challenges and especially regarding contamination.

With previous generations of lithography, a mask may be cleaned, then inspected, and then covered with a pellicle, then inspected again. However, the illumination with these shorter wavelengths of light may not be able to easily follow this procedure. At the present time, there are few or no materials that can adequately withstand radiation from the lower wavelength (e.g. 157 nm) light. Another problem, however, is that even if a cover could be added, contamination could still exist when the conventional system of cleaning and testing was used.

BRIEF DESCRIPTION OF THE DRAWINGS

These and other aspects will now be described in detail with reference to the accompanying drawings, wherein.

DETAILED DESCRIPTION

Many materials on a mask are transparent or otherwise non-problematic at the usual visible/ultraviolet wavelengths that are used to inspect the mask. However, the inventors found that those same contaminants became opaque at lower wavelengths such as 157 nm. Accordingly, the usual technique of inspecting masks did not adequately detect these materials.

For example, the present inventors have found that certain contaminants including alkenes, water, less conjugated aromatic systems, ketones and aldehydes may be transparent when inspected using visible or ultraviolet inspection wavelengths. However, the same materials may be absorbing at 157 nm.

The present system uses a technique that can detect a wide range of molecular species on the mask, including species that may be unnoticed at visible and/or ultraviolet wavelengths. The detection scheme uses both infrared absorption and Raman light scattering technique to detect materials of different types on the mask surface. Each technique may detect different organic or inorganic species by their interaction with the electric field.

Figure 1:
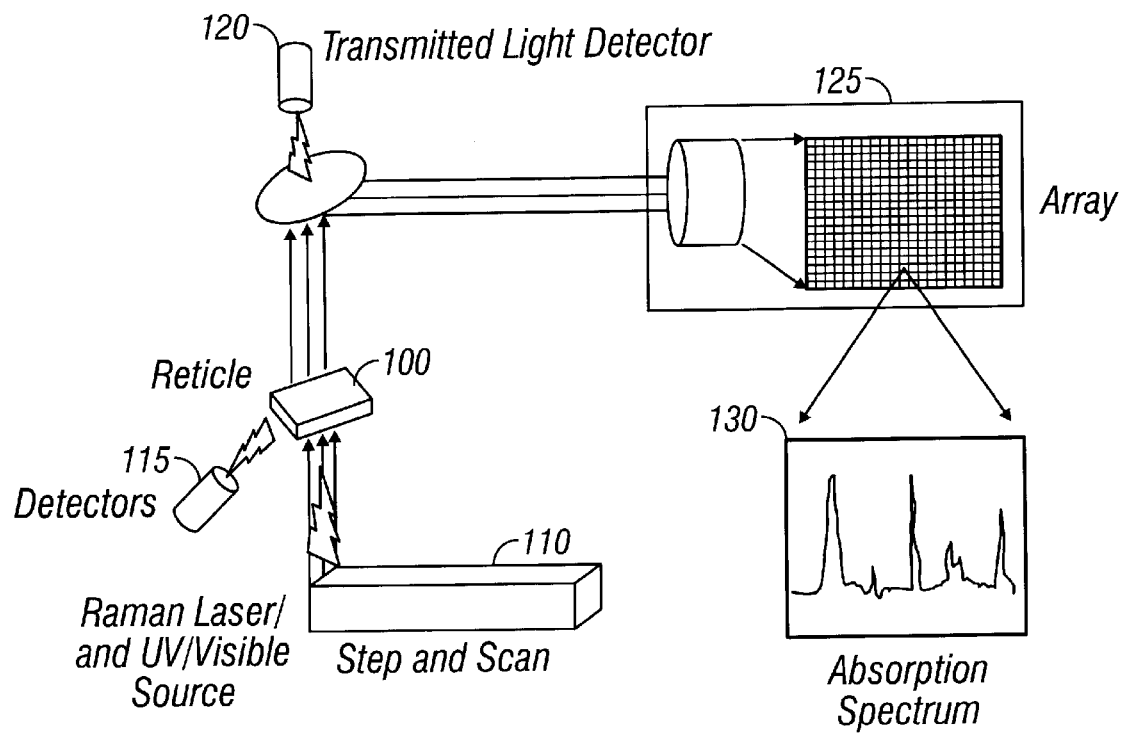
FIG. 1 shows a block diagram of the present system.

FIG. 1 shows a block diagram of a defect inspection tool for a mask. This technique uses vibrational spectroscopy. Two kinds of vibrational spectroscopy are used. A first uses infrared absorption spectroscopy. The second uses Raman light scattering spectroscopy. The IR technique uses molecules which have a permanent dipole moment which interacts with the incident radiation. Some examples include molecules may absorb a photon which is resonant from the incident radiation, that photon being one which causes a particular vibrational transition in the molecule. For example, particular functional groups in the molecule may absorb light of certain frequencies. The frequencies are substantially the same from compound to compound although minor shifts in wavelength may be seen depending on the rest of the compounds. For example, the OH group may absorb at between 3200 and 3600 $cm^{-1}$. The C=O group of ketones may absorb at 1710 $cm^{-1}$. The $CH_3$ group may absorb at between 1450 $cm^{-1}$ and 1375 $cm^{-1}$.

Additional advantages may be obtained by using two different processes: each of which have different ways of interacting with the contaminant in a way that does not depend on the visible light passing characteristics of the contaminant. In this way, the different ways may detect different contaminants.

Raman spectroscopy is a complementary technique to IR absorption, but differs in that the molecule need not possess a permanent dipole moment. A dipole moment is induced when the electric field interacts with the molecule, leading to an inelastic scattering event characteristic of the molecular vibration.

Surface sensitivity can be improved in this system by tuning the laser frequency. For example, if a tunable laser is used, then the laser may be scanned over the frequencies of interest, and the best frequency found.

A block diagram of the system is shown in FIG. 1. A reticle 100 forms the item to be tested. The reticle is illuminated by a test jig 110 which includes a Raman laser, and an IR source. The Raman laser and IR source are scanned across the area of interest. Light scattering due to particles on the surface is detected by detectors 115 and 116. The back scattered light is collected by the detector and can be resolved by appropriate processing algorithms. The contents of the absorption spectrum shown at 130 may indicate the presence of contaminants on the surface of the reticle.

By using both Raman spectroscopy and infrared spectroscopy at the same time, a wide variety of different kinds of contaminants can be detected.

Figure 2:
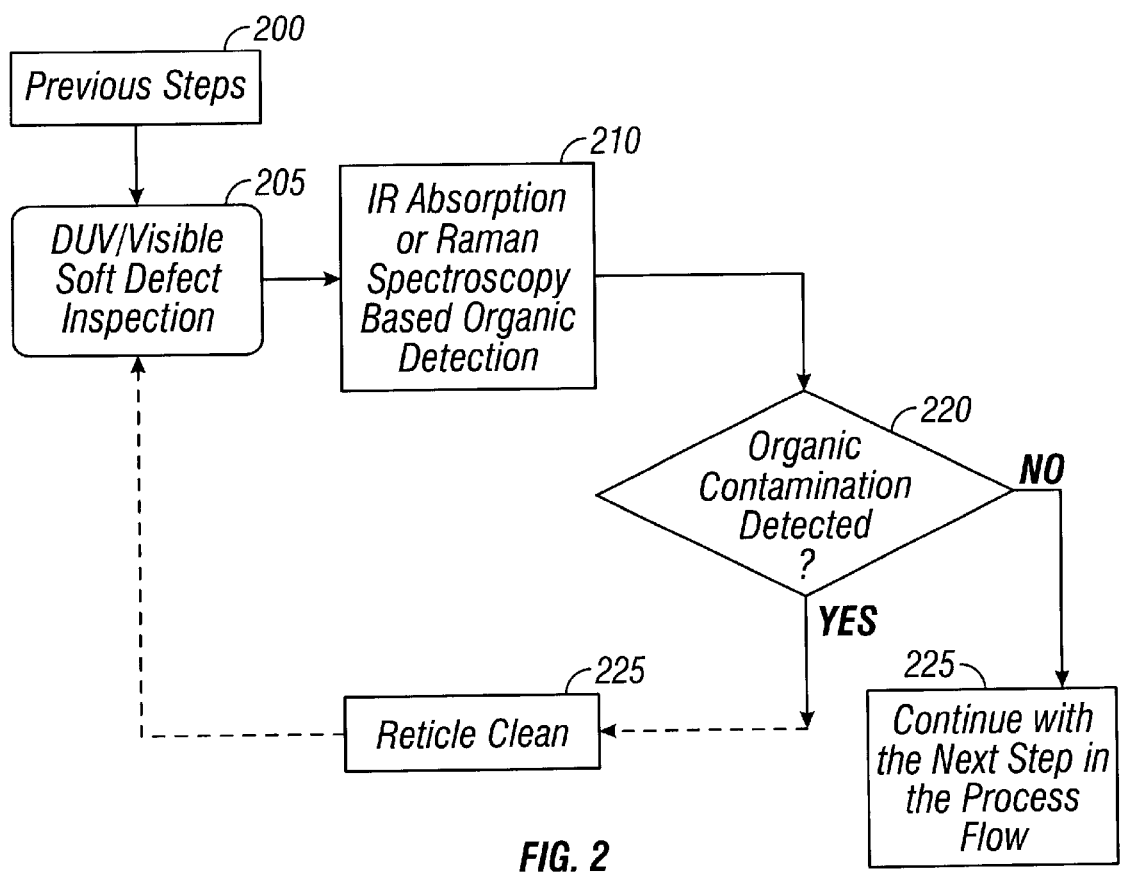
FIG. 2 shows a flowchart of operation.

The system in FIG. 1 follows the process flowchart of FIG. 2. At 200, defect detection and cleaning are carried out. These may use visible or deep ultraviolet light for defect detection. These steps still may be useful, since they may identify and/or remove certain kinds of contaminants. 205 detects the soft defects in this way. However, as described above, other contaminants may still remain, i.e. those which cannot be seen based on visible or UV radiation, but are visible or opaque under 157 nm radiation.

At 210, IR absorption and Raman spectroscopy-based organic detection are used in combination. The spectrum is analyzed at 220, and organic contaminants are detected. The analysis of the spectrum may comprise obtaining a spectrum of a completely clear and clean mask.

Figure 3A:
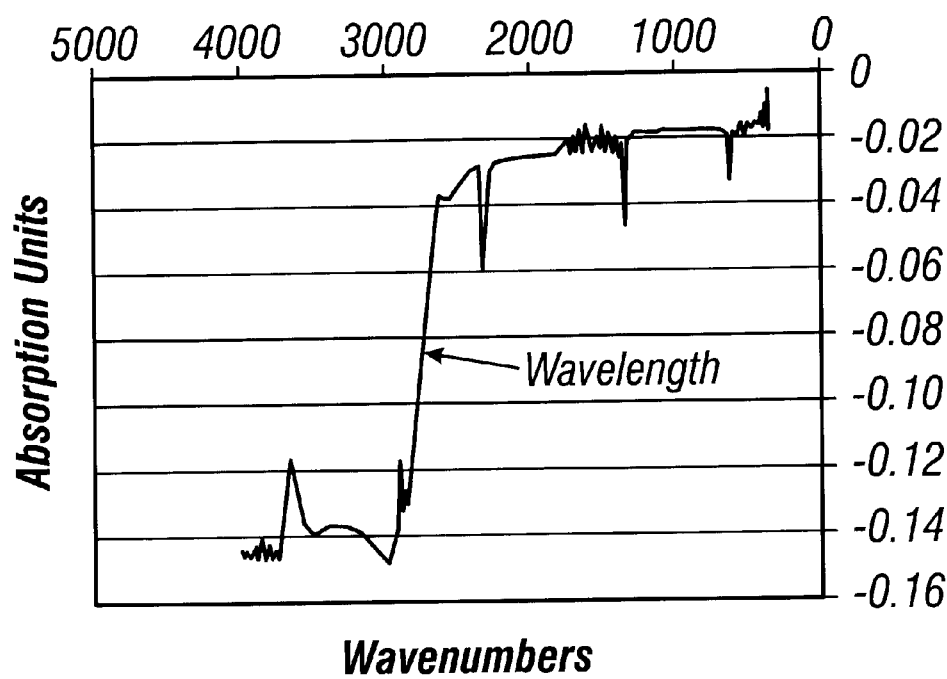
FIGS. 3A–3D Show alternative spectra of different scenarios of scanning the glass.
Figure 3B:
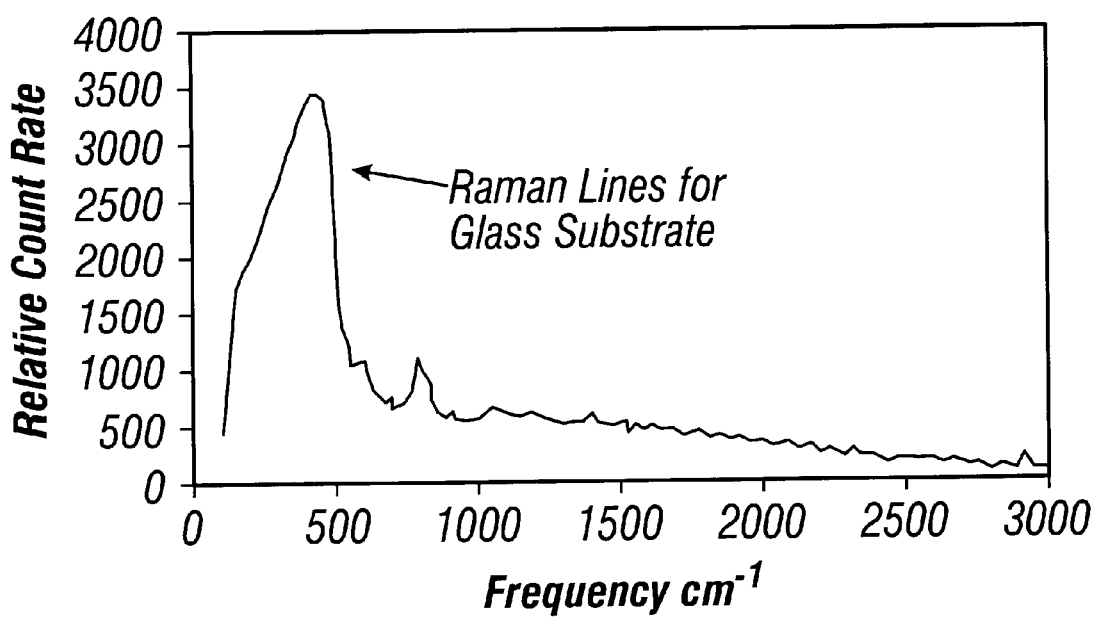
Figure 3C:
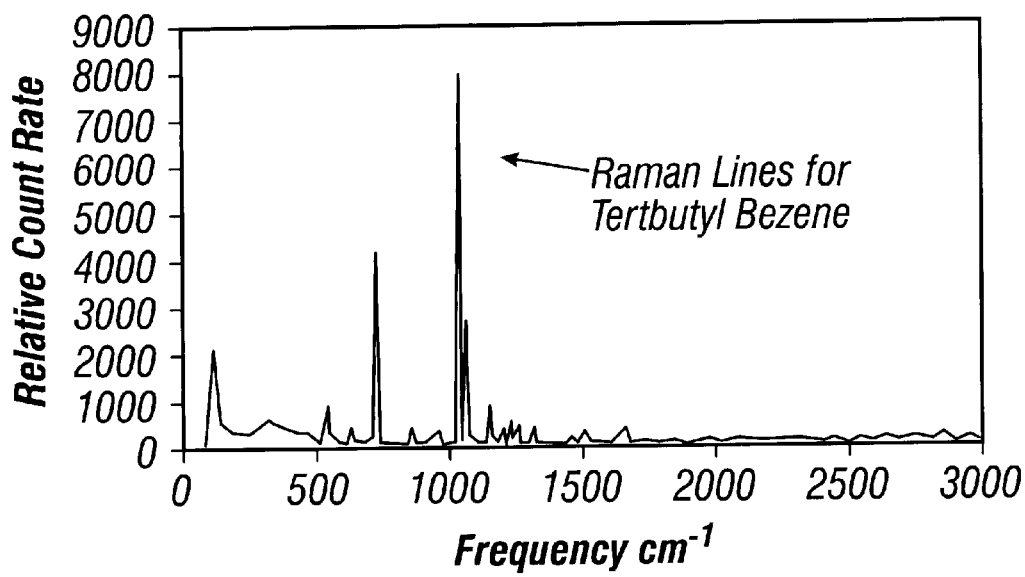

A number of different spectra are shown in FIGS. 3A–3B. For example, the spectrum shown in FIG. 3C is a spectrum of pure $SiO_2/F$ glass. The mask with the contaminants is analyzed. This may obtain, for example, different spectra.

Figure 3D:
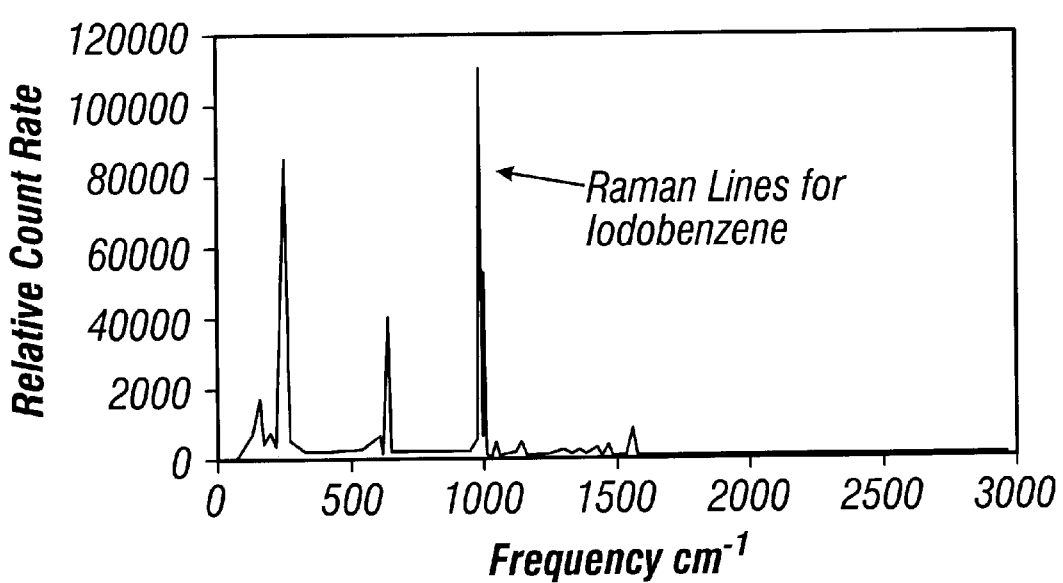

A background-subtracted transmission spectrum of ethanol and t-butyl benzene in which the absorption units have been obtained from the reflection units, is shown in FIG. 3A. The Raman spectrum is shown in FIGS. 3C–3D. Each of the spectra can be used to detect the presence of contaminants.

If organic contaminants are detected at 220, then another cleaning process is carried out at 225, followed by flow returning to 205 to carry out the UV, visible, IR absorption, and Raman spectroscopy tests.

If no organic contamination is detected at 220, the system continues with the next step in the process flow at 225.

FIGS. 3A–3D show examples of the wavelength resolved vibrational spectra of the different molecular species on fused silica glass using Raman and IR spectroscopy. FIG. 3A shows a grazing incidence background subtracted IR spectrum of a sample of ethanol and tertiary butyl benzene on glass which was collected after plating. FIG. 3B shows a Raman spectrum of $SiO_2$/F. glass. FIG. 3C shows the tert butyl benzene after background subtraction. FIG. 3D shows Raman spectrum of iodobenzene on the glass after background subtraction.

Although only a few embodiments have been disclosed in detail above, other modifications are possible. For example, other low wavelength light may have similar problems. Any wavelengths which are lower than 200 nm, e.g., 193 nm, 157 nm, 126 nm etc specifically lower than 157 nm may have similar problems. All such modifications are intended to be encompassed within the following claims, in which:

What is claimed is:

1. A testing method, comprising:
   testing a lithography mask using a combination of Raman techniques and infrared absorption techniques; and
   using said testing to detect contaminants on said mask, including contaminants which may be substantially transparent at ultraviolet and visible wavelengths, wherein said lithography is carried out using 157 nm light, wherein said using comprises determining materials which are transparent at visible and ultraviolet inspection wavelengths, but opaque at 157 nm.

2. A method as in claim 1, further comprising using said mask for lithography, after said testing.

3. A testing method, comprising:
   testing a lithography mask using a combination of Raman techniques and infrared absorption techniques; and
   using said testing to detect contaminants on said mask, including contaminants which may be substantially transparent at ultraviolet and visible wavelengths, wherein said testing comprises first testing a known cleaned mask, to determine a background spectrum, and second testing a mask to be tested, and subtracting said background spectrum to obtain a resultant absorption spectrum.

4. A testing method, comprising:
   testing a lithography mask using a combination of Raman techniques and infrared absorption techniques; and
   using said testing to detect contaminants on said mask, including contaminants which may be substantially transparent at ultraviolet and visible wavelengths, wherein said lithography is carried out using 157 nm light, wherein said using comprises determining materials which are transparent at visible and ultraviolet inspection wavelengths, but opaque at 157 nm, wherein said testing comprises detecting scattered light and detecting transmitted light.

5. A testing method, comprising:
   testing a mask using a first technique which uses a first kind of light to detect interaction with dipole moments of elements on the surface of said mask which comprises finding contaminants which are transparent under one of visible and/or ultraviolet light; and
   testing said mask using a second technique simultaneously with the first technique which comprises finding contaminants which are transparent under one of visible and/or ultraviolet light, using a second kind of light different than the first kind of light.

6. A method as in claim 5, wherein said first kind of light is infrared light.

7. A method as in claim 6, wherein said second kind of light is laser light.

8. A method as in claim 5, wherein said first kind of light is laser light.

9. A method as in claim 5, wherein said first technique includes infrared absorption spectroscopy.

10. A method as in claim 9, wherein said second technique includes Raman spectroscopy.

11. A method as in claim 5, further comprising analyzing said spectrum to be analyzed by comparing said spectrum against other spectra including spectra of possible contaminants.

12. A method, comprising:
    using both of a predetermined first and second measuring techniques to detect spectra of a plurality of different contaminants which are transparent at visible wavelengths, but which are detectable at lower than visible wavelengths to obtain spectra; and
    comparing said spectra against said spectra of said plurality of different contaminants.

13. A method as in claim 12, wherein said comparing comprises subtracting a background spectra from an acquired spectra, prior to said comparing.

14. A method as in claim 12, wherein said contaminants include water.

15. A method as in claim 12, wherein said wavelength lower than visible includes a wavelength which is less than 200 nm.

16. A method as in claim 15, wherein said wavelength lower than visible is 157 nm.

17. A tasting system, comprising:
    a light source which produces a Raman laser and an infra red absorption spectroscopy output; and
    a detector which subtracts a background spectra from an acquired spectra, and detects a result of both IR absorption and Raman spectroscopy on a sample.

18. A system as in claim 17, further comprising an element which forms an absorption spectrum based on a result of said detector.

19. A system as in claim 17, wherein said sample is a lithography mask.

20. A method comprising:
    inspecting a mask surface using a first technique that does not depend on interacting with any material on the mask surface in a way that depends on the visible light passing characteristics of the material; and
    also inspecting said mask surface using a second technique where the surface is visually inspected and testing a mask which is clean, to obtain a spectrum therefrom, and subtracting said spectrum form a final spectrum, to from a spectrum to be analyzed.

21. A method as in claim 20, wherein said first technique includes a first detecting and a second detecting using a different operation than said first detecting.

22. A method as in claim 20, wherein said first detecting and said second detecting each detect a dipole reaction of said material.

23. A method as in claim 22, wherein said first detecting is infrared absorption, and said second detecting is Raman spectroscopy.

24. A testing method, comprising:
    testing a mask using a first technique which uses a first kind of light to detect interaction with dipole moments of elements on the surface of said mask which comprises funding contaminants which are transparent under one of visible and/or ultraviolet light;
    testing said mask using a second technique simultaneously with the first technique which comprises finding contaminants which are transparent under one of visible and/or ultraviolet light, using a second kind of light different than the first kind of light, and testing a mask which is clean, to obtain a spectrum therefrom, and subtracting said spectrum from a final spectrum, to form a spectrum to be analyzed.

* * * * *